(12) United States Patent
Baek

(10) Patent No.: US 12,109,350 B1
(45) Date of Patent: Oct. 8, 2024

(54) NASAL CATHETER TO PREVENT NEGATIVE PRESSURE

(71) Applicant: Young Jin Baek, Changwon-si (KR)

(72) Inventor: Young Jin Baek, Changwon-si (KR)

(*) Notice: Subject to any disclaimer, the term of this patent is extended or adjusted under 35 U.S.C. 154(b) by 0 days.

(21) Appl. No.: 18/525,883

(22) Filed: Dec. 1, 2023

(30) Foreign Application Priority Data

Jun. 19, 2023 (KR) .......................... 10-2023-0078098

(51) Int. Cl.
*A61M 1/00* (2006.01)

(52) U.S. Cl.
CPC ..................................... A61M 1/74 (2021.05)

(58) Field of Classification Search
CPC .. A61M 1/84; A61M 1/86; A61M 2210/0618; A61M 1/74
See application file for complete search history.

(56) References Cited

U.S. PATENT DOCUMENTS

| | | | |
|---|---|---|---|
| 7,458,956 B1* | 12/2008 | Adams | A61M 25/0082 604/158 |
| 10,973,960 B2* | 4/2021 | Mehta | A61M 1/86 |
| 11,207,057 B1* | 12/2021 | Vu | A61M 3/0287 |
| 2009/0281454 A1* | 11/2009 | Baker | A61M 1/82 600/573 |
| 2012/0150119 A1* | 6/2012 | Schaeffer | A61B 17/3415 604/164.11 |
| 2017/0119513 A1* | 5/2017 | Decherf | A61D 19/04 |

FOREIGN PATENT DOCUMENTS

| | | | |
|---|---|---|---|
| JP | 5993645 B2 | * | 9/2016 |
| KR | 20-1998-0055806 U | | 10/1998 |
| KR | 10-2002-0080596 A | | 10/2002 |
| KR | 10-2010-0017248 A | | 2/2010 |
| KR | 10-2012-0008633 A | | 2/2012 |
| KR | 10-2014-0016721 A | | 2/2014 |
| KR | 10-1492804 B1 | | 2/2015 |
| KR | 5993645 B2 | | 9/2016 |
| KR | 20-2022-0002082 U | | 8/2022 |
| KR | 20220002082 U | * | 8/2022 |
| KR | 10-2540159 B1 | | 6/2023 |

* cited by examiner

*Primary Examiner* — Scott J Medway
(74) *Attorney, Agent, or Firm* — Revolution IP, PLLC

(57) ABSTRACT

The present invention relates to a nasal catheter to prevent a negative pressure, and more particularly, to a nasal catheter that prevents a negative pressure which includes a tube body which is connected to one end of a shaft of an aspirator that suctions rhinorrhea or secretions, and is made up of a cone part whose diameter increases from a distal end toward a rear end of the conduit and an extension part that forms a passage extending from the cone part, and is inserted into the nasal cavity; and a ventilation part in which a ventilation hole penetrating from the distal end of the cone part toward the rear end is formed to allow outside air to flow into the nasal cavity.

3 Claims, 7 Drawing Sheets

NASAL CATHETER TO PREVENT NEGATIVE PRESSURE

CROSS-REFERENCE TO RELATED APPLICATION

This application claims under 35 U.S.C. § 119 (a) the benefit of Korean Patent Application No. 10-2023-0078098 filed on Jun. 19, 2023, the entire contents of which are incorporated herein by reference.

BACKGROUND

(a) Technical Field

The present invention relates to a nasal catheter to prevent a negative pressure, and more specifically, to a nasal catheter to prevent a negative pressure, which has a ventilation part that allows outside air to flow into a tube body so as not to occur a sealing phenomenon of an interior of a nasal cavity when inserting the tube body into a nasal cavity to suction with a negative pressure.

(b) Background Art

In general, a suction catheter is used to suction secretions (including accumulations, hereinafter the same) contained in a body cavity of a human or animal and take them out of the body using a vacuum device or the like.

A conventional suction catheter includes a tube body, a rounded guide part integrally formed at a distal end of the tube body, and an adapter integrally formed at a rear end of the tube body. One or two suction holes are usually formed in a region of the tube body adjacent to the guide part.

As an example, when the guide part is placed in the throat and a vacuum device connected to the adapter is activated, phlegm exits the throat through the suction hole. Furthermore, it can be inserted into the human body's urethra and used to remove urine collected in the bladder.

However, in the conventional suction catheter having the above-mentioned structure, a small number of suction holes are formed only in the region of the tube body adjacent to the guide part, and thus there is a problem that suction pressure is concentrated, resulting in a problem of damage to internal tissues of the body.

In addition, there is a problem that a space between the distal end of the tube body and the suction hole is closed, and thus a portion of the tube body corresponding to a length between the distal end of the tube body and the suction hole is not utilized for suction action, and the suction catheter needs to be inserted deeper into the human body by that length.

Furthermore, in recent years, attempts to use suction catheters have been made to remove secretions within the nasal cavity, which may further cause problems of conventional suction catheters as described above.

In particular, purulent rhinorrhea inside the nasal cavity requires removal and cleaning because residues caused by inflammation lead to the growth of bacteria and the development of infection.

When suctioning rhinorrhea with the catheter, if an area extending from the nose to the neck (choanae and nasopharynx) is swollen or narrowed, and thus the air corresponding to the volume to be suctioned does not flow in, a negative pressure is formed in the nasal cavity and suction is not possible.

PRIOR ART DOCUMENTS

Patent Document (Patent Document 1) Korean Laid-open Patent Publication No. 10-2012-0008633 (published on Feb. 1, 2012)

SUMMARY OF THE DISCLOSURE

In order to solve the above-mentioned problems of the related art, the present invention provides a nasal catheter with a new structure to prevent a negative pressure, which has a ventilation part that allows outside air to flow into a tube body so as not to occur a sealing phenomenon of an interior of a nasal cavity when inserting the tube body into the nasal cavity to suction with a negative pressure.

In addition, the present invention provides a nasal catheter to prevent a negative pressure by controlling the inflow of air into the ventilation part depending on whether the posterior nasal passage is blocked.

Further, the present invention provides a nasal catheter to prevent a negative pressure by forming at least one opening communicating with the ventilation part to connect a hose that can supply moisture into the nasal cavity.

To solve the above problems,
the present invention provides a nasal catheter to prevent a negative pressure, including:
a tube body which is formed as a conduit connected to one end of a shaft provided in an aspirator that suctions rhinorrhea or secretions and takes them out of the body, and is made up of a cone part whose diameter increases from a distal end toward a rear end of the conduit and an extension part that forms a passage extending from the cone part, and is inserted into the nasal cavity; and
a ventilation part in which a ventilation hole penetrating from the distal end of the cone part toward the rear end is formed to allow outside air to flow into the nasal cavity.

In an embodiment of the present invention, it can be characterized in that the ventilation part increases a suction force that causes rhinorrhea or secretions inside the nasal cavity to flow into the inside of the tube body, when one end of the ventilation hole located at the rear end of the cone part is closed.

An embodiment of the invention may include:
a tube body which is formed as a conduit connected to one end of a shaft provided in an aspirator that suctions rhinorrhea or secretions and takes them out of the body, and is made up of a cone part whose diameter increases from a distal end toward a rear end of the conduit and an extension part that forms a passage extending from the cone part, and is inserted into the nasal cavity; and
a ventilation part which is formed as an inflow tube formed from an empty-internal tube, one end of which is located at the distal end of the cone part and the other end of which is located on one side of the extension part, and has an inflow hole which is bent and penetrates from the other end of the inflow tube to the outer surface of the extension part to allow outside air to flow into the nasal cavity.

In an embodiment of the present invention, it can be characterized in that the ventilation part increases a suction force that causes rhinorrhea or secretions inside the nasal cavity to flow into the inside of the tube body, when the inflow hole is closed.

In an embodiment of the present invention, an inclined part may be included, which reduces pressure of air suctioned into the distal end of the cone part by forming an inclination inside the distal end of the cone part.

An embodiment of the invention may include an opening in which at least one hole communicating with the ventilation part is formed on the outer surface of the cone part.

The nasal catheter to prevent a negative pressure according to the present invention has an advantage that allows an outside air to flow into the tube body so that when the tube body is inserted into the nasal cavity and suctioned with the negative pressure, the sealing phenomenon of interior of the nasal cavity does not occur, and increases the suction of rhinorrhea and secretions inside the nasal cavity.

In addition, the present invention has an advantage of allowing air to flow into the nasal cavity and facilitating drainage of nasal mucus, when the passage in the posterior nostril of the nasal cavity is blocked by rhinorrhea or edema of inflammatory tissue.

In addition, the present invention has an advantage that the suction force of the catheter can be controlled by controlling the inflow of air into the ventilation part depending on whether the posterior nasal passage is blocked.

In addition, the nasal catheter to prevent a negative pressure according to the present invention has an advantage that can connect a hose for supplying moisture into the nasal cavity, by forming at least one opening communicating with the ventilation part.

DETAILED DESCRIPTION

Figure 1:
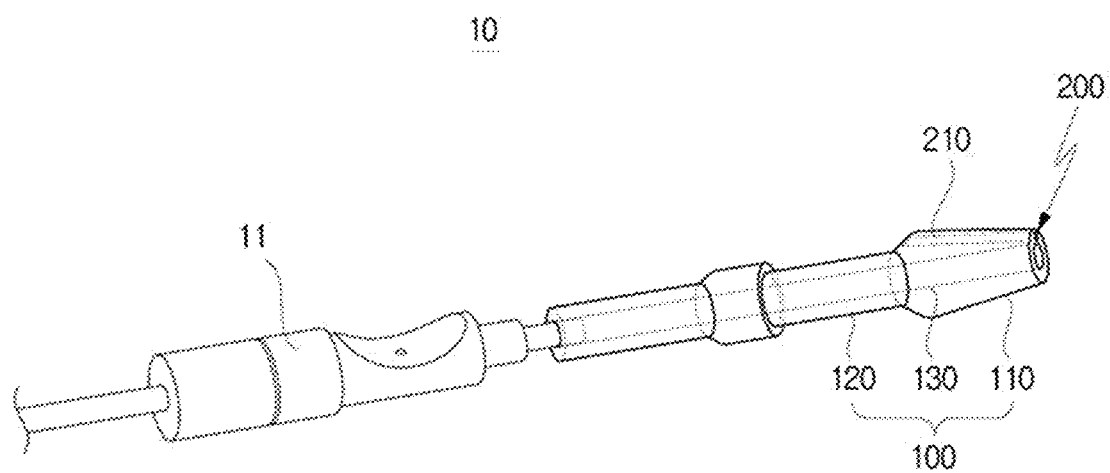
FIG. 1 is a perspective view illustrating an external shape of a nasal catheter to prevent a negative pressure according to an embodiment of the present invention.

Hereinafter, preferred embodiments will be described in detail with reference to the accompanying drawings, which will enable those skilled in the art to easily carry out the invention. However, in describing the operating principle of the preferred embodiment of the present invention in detail, when it is determined that a specific description of related known functions or configurations may unnecessarily obscure the gist of the present invention, detailed explanation thereof will be omitted.

Also, the same reference numerals are used throughout the drawings for parts having similar functions and actions.

In addition, in the entire specification, when a certain part is "connected" to another part, this includes not only a case of being directly connected, but also a case of being indirectly connected with another component in between. Furthermore, unless there is a specific statement to the contrary, the term "including" a certain component does not exclude other components, but means that other components may be further included.

Hereinafter, a nasal catheter to prevent a negative pressure according to a preferred embodiment of the present invention will be described in detail with reference to the accompanying drawings.

Figure 2:
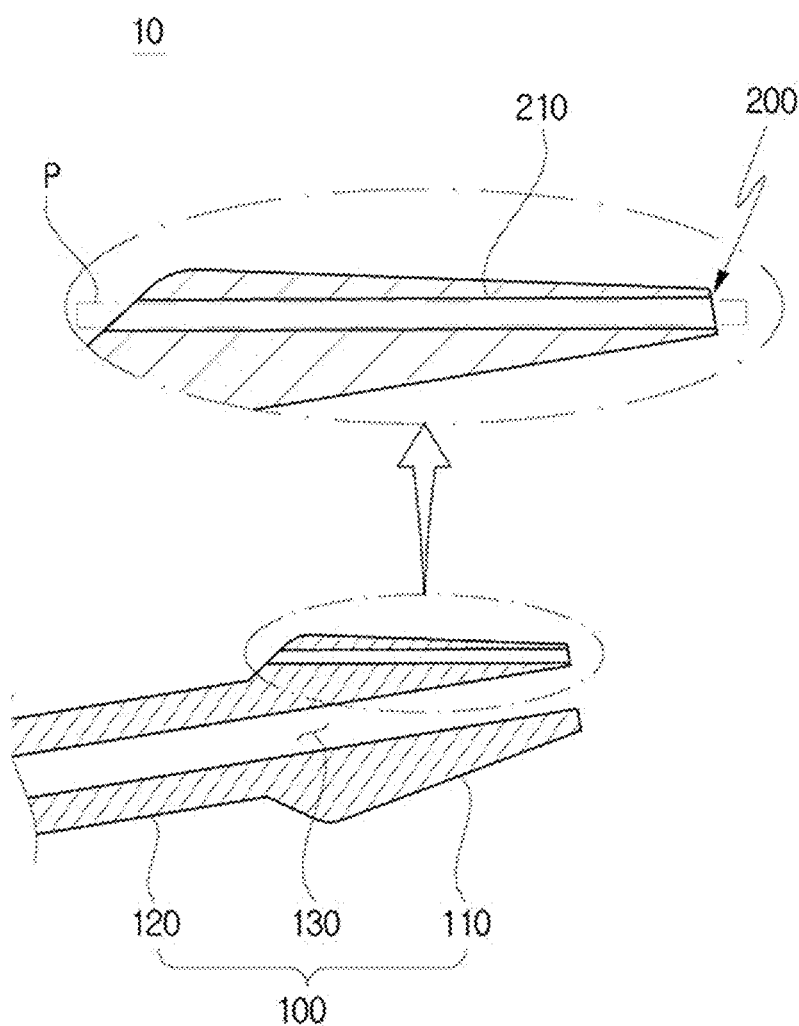
FIG. 2 is a partially enlarged cross-sectional view of the nasal catheter to prevent a negative pressure according to an embodiment of the present invention.
Figure 3:
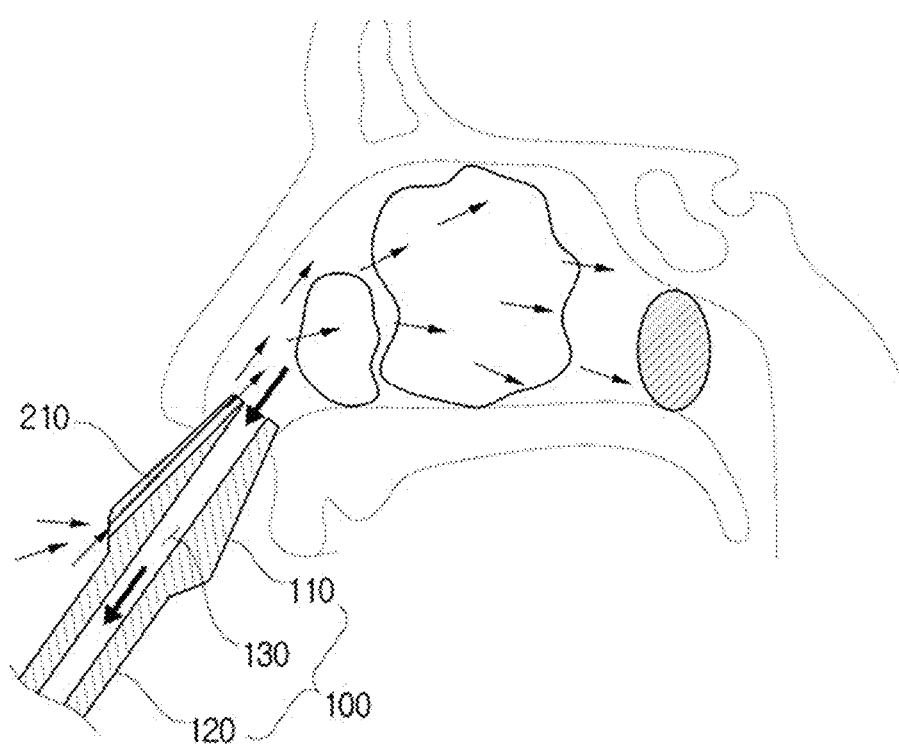
FIGS. 3 and 4 are exemplary diagrams illustrating the concept of the nasal catheter to prevent a negative pressure according to an embodiment of the present invention.
Figure 4:
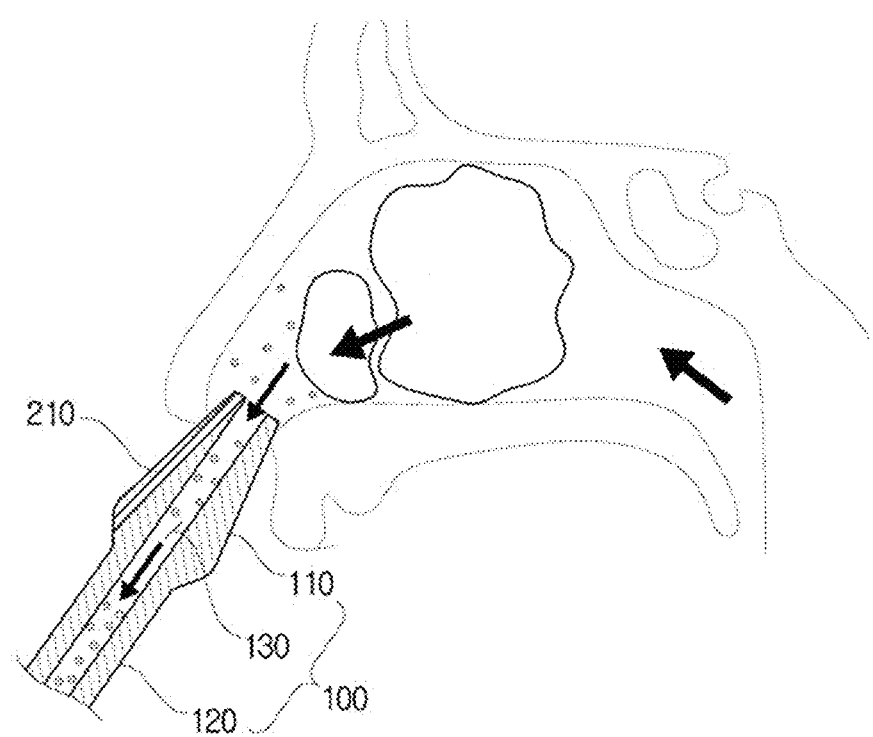
Figure 5:
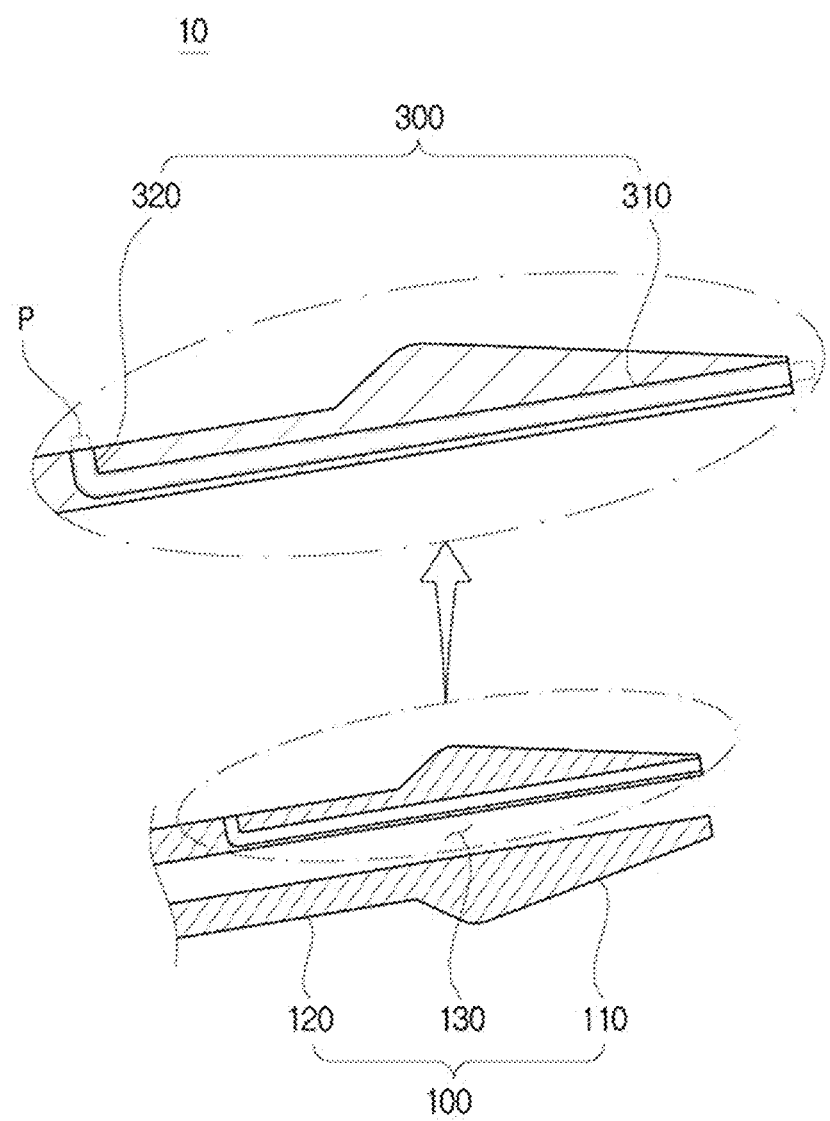
FIG. 5 is a partially enlarged cross-sectional view illustrating the nasal catheter to prevent a negative pressure according to an application example of the present invention.
Figure 6:
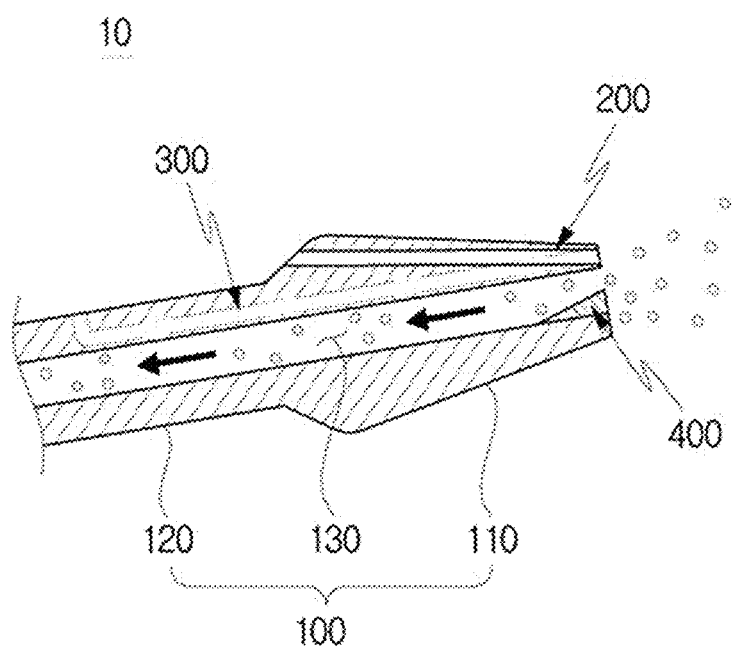
FIG. 6 is an exemplary cross-sectional view illustrating an inclined part of the nasal catheter to prevent a negative pressure according to an embodiment of the present invention.
Figure 7:
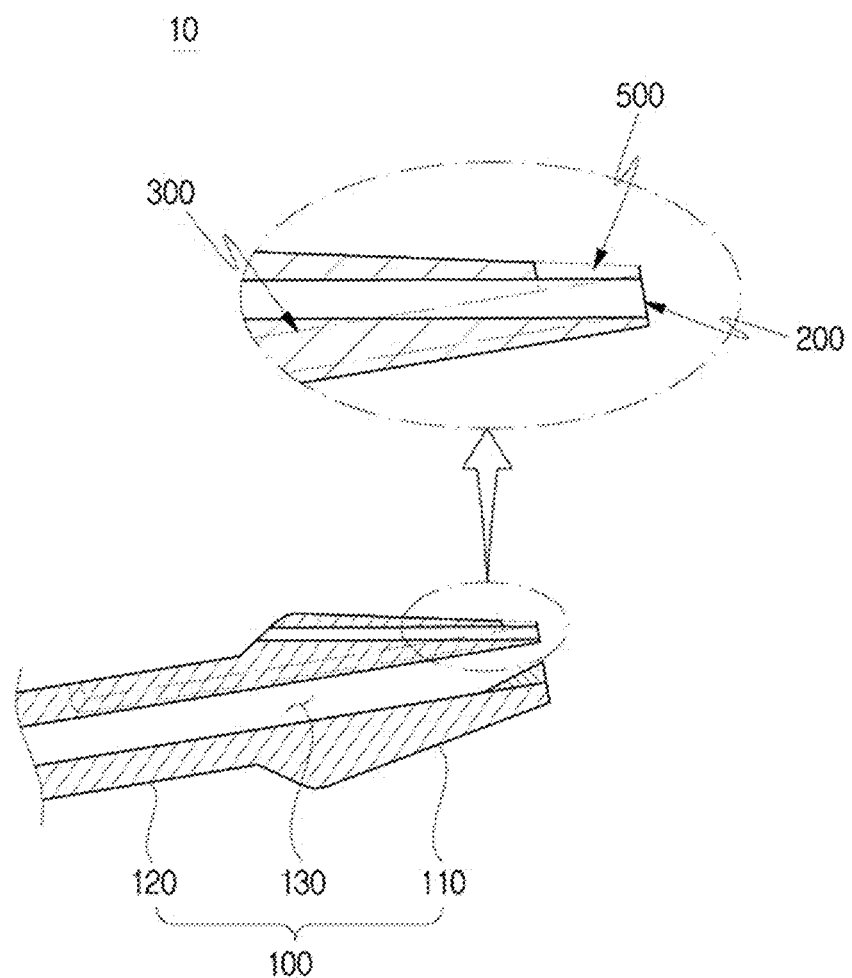
FIG. 7 is an exemplary cross-sectional view illustrating an opening of the nasal catheter to prevent a negative pressure according to an embodiment of the present invention.

FIG. 1 is a perspective view illustrating an external shape of a nasal catheter to prevent a negative pressure according to an embodiment of the present invention. FIG. 2 is a partially enlarged cross-sectional view of the nasal catheter to prevent a negative pressure according to an embodiment of the present invention in a cross-section. FIGS. 3 and 4 are exemplary diagrams illustrating the concept of the nasal catheter to prevent a negative pressure according to an embodiment of the present invention. FIG. 5 is a partially enlarged cross-sectional view of the nasal catheter to prevent a negative pressure according to an application example of the present invention. FIG. 6 is an exemplary cross-sectional view of an inclined part of the nasal catheter to prevent a negative pressure according to an embodiment of the present invention in a cross-section. FIG. 7 is an exemplary cross-sectional view illustrating an opening of the nasal catheter to prevent a negative pressure according to an embodiment of the present invention.

As shown in FIG. 1, a nasal catheter 10 to prevent a negative pressure according to an embodiment of the present invention includes a tube body 100 and a ventilation part 200.

More specifically, as shown in FIGS. 1 and 2, the nasal catheter 10 to prevent the negative pressure according to an embodiment of the present invention includes a tube body 100 which is formed as a conduit connected to one end of a shaft 11 provided in an aspirator that suctions rhinorrhea or secretions and takes them out of the body, and is made up of a cone part 110 whose diameter increases from the distal end toward the rear end of the conduit and an extension part 120 that forms a passage 130 extending from the cone part 110, and is inserted into the nasal cavity, and a ventilation part 200 in which a ventilation hole 210 penetrating from the distal end of the cone part toward the rear end is formed to allow outside air to flow into the nasal cavity.

Here, the aspirator is a device that suctions nasal mucus with negative pressure, and is generally used to suction rhinorrhea or secretions in a patient's nasal cavity in a medical facility such as otolaryngology. That is, it is a mechanical device that suctions rhinorrhea or secretions from the body and takes it out of the body.

Referring to FIGS. 1 and 2, the tube body 100 is formed as a conduit that is flexible and open on both sides so that it can be inserted inside the nasal cavity. Then the tube body is connected to one end of the shaft 11 of the rhinorrhea or secretion aspirator.

The cone part 110 is formed with an extension part 120 whose diameter gradually increases from the distal end toward the rear end and is connected to one end of the shaft 11.

That is, the cone part 110 is formed to have a small diameter in order to insert the distal end into the nasal cavity, and has a shape that increases in diameter toward the rear end to prevent excessive insertion into the nasal cavity. Further, it is preferable for the cone part to have a certain elasticity in order to maintain its shape inside the nasal cavity.

The passage 130 allows the distal end of the cone part 110 to the rear end and the extension part 120 thereof to communicate with each other, so that rhinorrhea, secretions or nasal mucus can be suctioned to the distal end of the cone part 110 by the operation of the aspirator.

Referring to FIGS. 2 and 3, the ventilation part 200 forms a ventilation hole 210 penetrating from the distal end to the rear end of the cone part 110 to serve to allow outside air to flow into the nasal cavity.

For example, when a conventional nasal catheter is inserted into the nose to suction rhinorrhea, secretions or nasal mucus inside the nasal cavity by operation of the aspirator, a negative pressure is generated and increases in the nasal cavity, causing a problem of poor in suction of rhinorrhea, secretions or nasal mucus. Continuous suction of the inside of the sealed nasal cavity can cause bleeding in the nasal septum and discomfort for the patient.

In addition, the ventilation hole 210 may form a separate tube P inserted therein to allow air to flow into the nasal cavity through the tube P. By opening and closing one end of the tube P, it is possible to control the suction force of rhinorrhea, secretions or nasal mucus flowing into the distal end of the cone part 110.

Therefore, as shown in FIGS. 3 and 4, the nasal catheter 10 to prevent a negative pressure according to the embodiment of the present invention forms the ventilation part 200 having a ventilation part hole 210 formed therein to allow outside air to flow into one side of the tube body 100 inserted into the nasal cavity. Then, when the aspirator is operated to suction rhinorrhea or secretions, the inflow of air lowers the negative pressure in the nose and induces the smooth suction.

In addition, as shown in FIG. 3, if the passage is blocked by rhinorrhea or edema of inflammatory tissue in the posterior nostril inside the nasal cavity, when operating the aspirator, the negative pressure in the nose is further increased, and suction may not be smooth.

Therefore, as described above, when outside air flows into one side of the tube body 100 inserted into the nasal cavity through the ventilation part 200 having the ventilation hole 210 formed therein, and the aspirator is operated to suction rhinorrhea or secretions, as shown in FIG. 4, the negative pressure becomes lower and the rhinorrhea or secretions can be suctioned through the tube body 100.

In this case, sticky nasal mucus generated due to rhinorrhea or edema of inflammatory tissue in the nasal cavity moves around the distal end of the tube body 100 and can be discharged from interior of the nasal cavity to the outside.

This is because when the aspirator is operated, outside air flows into the nasal cavity by the amount that the rhinorrhea, secretions or nasal mucus are suctioned.

On the other hand, in the nasal catheter 10 to prevent a negative pressure according to the embodiment of the present invention, when the ventilation part 200 closes one end of the ventilation hole 210 located at the rear end of the cone part 110, it serves to increase the suction force that allows the rhinorrhea or secretions inside the nasal cavity to flow into the tube body 100.

That is, the ventilation part 200 lowers the negative pressure in the nasal cavity to generate a suction force, but when the suction force becomes weak and thus the rhinorrhea or secretions are not removed smoothly, the ventilation part 200 can temporarily close the ventilation hole 210 to increase the negative pressure inside the nasal cavity. Accordingly, the rhinorrhea or secretions located inside the sealed nasal cavity can be moved to the distal end of the cone part 110 and moved to the aspirator through the interior of the extension part 120.

In this way, it is also possible to control the negative pressure by opening and closing one end of the ventilation hole 210 to control the inflow of air.

As shown in FIG. 5, a nasal catheter 20 to prevent a negative pressure according to the application example of the present invention includes a tube body 100 which is formed of a conduit connected to one end of a shaft 11 provided in an aspirator that suctions rhinorrhea or secretions and takes them out of the body, and is made up of a cone part 110 whose diameter increases from the distal end toward the rear end of the conduit and an extension part 120 that forms a passage 130 extending from the cone part, and is inserted into the nasal cavity, and a ventilation part 300 which is formed as an inflow tube 310 formed from an empty-internal tube, one end of which is located at the distal end of the cone part 110 and the other end of which is located on one side of the extension part, and which has an inflow hole 320 which is bent and penetrates from the other end of the inflow tube to the outer surface of the extension part to allow outside air to flow into the nasal cavity.

Here, the tube body 100 is the same as the content described above, and thus detailed description thereof will be omitted.

Referring to FIG. 5, the ventilation part 300 is to allow outside air to flow into the nasal cavity through the cone part 110, and is formed from the distal end of the cone part 110 to one side of the extension part 120 to make it easier to open and close the inflow hole 320.

The inflow tube 310 is formed from an empty-internal tube, and has one end located at the distal end of the cone part 110 and the other end formed of a hole located on one side of the extension part 120. That is, the inflow tube 310 may be formed as a hole extending from the distal end of the cone part 110 to one side of the extension part 120 in a longitudinal direction, or may be formed as a separate tube P inserted into the hole.

The inflow hole 320 is bent and penetrated from the other end of the inflow tube 310 to the outer surface of the extension part 120, and allows the outer surface of the extension part 120 to communicate with the other end of the inflow tube 310.

Such a ventilation part 300 can increase the suction force that allows rhinorrhea or secretions inside the nasal cavity to flow into the tube body 100 when the inflow hole 320 is closed. A detailed explanation thereof will be omitted since it is the same as that of the ventilation part 200 described above.

Furthermore, by forming the inflow hole 320 on one side of the extension part 120, the ventilation part 300 is located at a distance apart from the patient's nose, so that a practitioner can more easily open and close the inflow hole 320.

Meanwhile, as shown in FIG. 6, the nasal catheter 10 to prevent a negative pressure according to an embodiment of the present invention may include an inclined part 400.

The inclined part 400 forms an inclination inside the distal end of the cone part 110 and serves to reduce the pressure of air suctioned into the distal end of the cone part 110.

As an example, when inserting the cone part 110 into the nasal cavity to operate the aspirator, if rhinorrhea or secretions move to the distal end of the cone part 110 and move excessively through the passage 130, a pressure also acts on a surface of the nasal septum in the distal direction of the cone part 110, and bleeding may occur. If a large amount of rhinorrhea or secretions flow into the distal end of the cone part 110 at once, the distal is blocked and thus suction may not become smooth.

Therefore, the inclined part 400 is formed inside the distal end of the tube body 100 forming either the ventilation part 200 or the other ventilation part 300, so that it is desirable to reduce the pressure of the air suctioned into the inside of the cone part 110, reduce the pressure applied to the nasal septum, and reduce the movement of large amounts of rhinorrhea or secretions at once.

In addition, as shown in FIG. 7, the nasal catheter 10 to prevent negative pressure according to one embodiment of the present invention may include an opening 500.

The opening 500 has at least one hole communicating with the ventilation part 200 on the outer surface of the cone part 110, and can communicate with the ventilation hole 210 or the inflow tube 310 by cutting the outside of the distal end of the cone part 110.

This opening 500 allows a hose for supplying moisture to be inserted into the interior of the ventilation hole 210 or the inflow tube 310 to supply moisture to the nasal cavity. Preferably, the moisture supply hose is located inside further than one surface of the distal end of the cone part 110 to prevent moisture from being directly sprayed outside the septum.

Further, it is more preferable to form at least one opening 500 on the outer surface of the cone part 110 to allow not only the moisture supply hose but also outside air to flow into the nasal cavity.

As described above, although preferred embodiments of the present invention have been described in the detailed description of the present invention, this is an illustrative description of the most preferred embodiment of the present invention, and does not limit the present invention. It goes without saying that anyone with ordinary knowledge in the technical field to which the present invention pertains can make various modifications and imitations without departing from the scope of the technical idea of the present invention.

Therefore, the scope of the present invention is not limited to the embodiments described above, but can be implemented in various forms of embodiment within the scope of the appended claims. It is considered that the claims of the present invention may be modified to various extents that can be modified by anyone with ordinary knowledge in the technical field to which the invention pertains without departing from the gist of the invention claimed in the claims.

DESCRIPTION OF SYMBOLS

10: Nasal catheter to prevent negative pressure
11: Shaft
100: Tube body
110: Cone part
120: Extension part
130: Passage
200: Ventilation part
210: Ventilation hole
300: Ventilation part
310: Inflow tube
320: Tube inflow hole
400: Inclined part
500: Opening

What is claimed is:

1. A nasal catheter to prevent a negative pressure, comprising:
    a tube body formed as a conduit connected to one end of a shaft provided in an aspirator that is configured to suction rhinorrhea or secretions and take the rhinorrhea or secretions out of a body, comprising:
        a cone part having a diameter which increases from a distal end of the conduit toward a rear end of the conduit; and
        an extension part which is connected to the cone part having a passage extending longitudinally within the extension part and is configured to be inserted into a nasal cavity; and
    a ventilation part comprising:
        an inflow tube formed with an empty interior, the inflow tube penetrating an interior of a cross-section of the cone part and the extension part from a distal end of the cone part toward one side of the extension part; and
        an inflow hole which is bent at the one side of the extension part communicating from one end of the inflow tube to an outer surface of the extension part to allow an external air to flow into the nasal cavity, wherein the cone part and the extension part fully cover the ventilation part except both open ends of the ventilation part,
    wherein the ventilation part increases a suction force that causes the rhinorrhea or secretions in the nasal cavity to flow into an inside of the tube body upon when one end of the inflow hole located at the distal end of the cone part is closed.

2. The nasal catheter to prevent a negative pressure according to claim 1, further comprising: an inclined part which reduces pressure of air suctioned into the distal end of the cone part by forming an inclination inside the distal end of the cone part.

3. The nasal catheter to prevent a negative pressure according to claim 1, further comprising: an opening communicating with the ventilation part formed on the outer surface of the cone part.

* * * * *